United States Patent [19]

Michaely et al.

[11] Patent Number: 4,586,954
[45] Date of Patent: May 6, 1986

[54] ARYLACRYL ALIPHATIC AMIDE HERBICIDAL COMPOUNDS AND METHODS OF USE

[75] Inventors: William J. Michaely, Richmond; Jeff K. Curtis, Berkeley, both of Calif.

[73] Assignee: Stauffer Chemical Co., Westport, Conn.

[21] Appl. No.: 740,601

[22] Filed: Jun. 3, 1985

[51] Int. Cl.$^4$ .................. A01N 43/40; A01N 43/36; A01N 37/34
[52] U.S. Cl. .......................... 71/94; 71/95; 71/105; 558/395; 546/226; 548/540
[58] Field of Search ............... 260/465 D; 71/105, 94, 71/95; 546/226; 548/540

[56] References Cited

U.S. PATENT DOCUMENTS

| | | | |
|---|---|---|---|
| 3,079,366 | 2/1963 | Boyle et al. | 260/465 D X |
| 3,656,932 | 4/1972 | Scheuermann et al. | 71/105 |
| 3,981,717 | 9/1976 | Walworth | 71/105 |

Primary Examiner—Dolph H. Torrence
Attorney, Agent, or Firm—Michael J. Bradley

[57] ABSTRACT

A compound having the structural formula

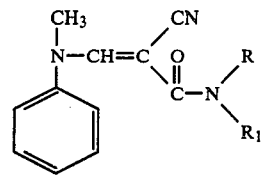

wherein
R is $C_1$–$C_8$ aliphatic and cycloaliphatic, $C_2$–$C_3$ haloaliphatic, $C_2$–$C_4$ alkoxyalkyl, —$CH_2CN$, —$CH(CH_3)CN$ or —$C(CH_3)_2CN$;
$R_1$ is hydrogen or $C_1$–$C_3$ alkyl, provided that R and $R_1$ cannot both equal hydrogen at the same time; or
R and $R_1$ taken together form a $C_4$–$C_6$ alkyl or heteroalkyl ring which may be lower alkyl substituted wherein the hetero atom is oxygen or nitrogen, and the herbicidal use of the compound.

31 Claims, No Drawings

ARYLACRYL ALIPHATIC AMIDE HERBICIDAL COMPOUNDS AND METHODS OF USE

BACKGROUND OF THE INVENTION

The present invention relates to certain arylacryl aliphatic amide compounds which are useful as post-emergent herbicides against annual and perennial grasses and broadleaf weeds.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants fom the soil, and the post-emergence herbicides are normally applied to plant surfaces after emergence of the weeds or other unwanted plants from the soil.

THE PRIOR ART

Many arylacryl esters have been disclosed in the prior art [Huppatz, John L. et al., *Agric. Biol. Chem.*, 1982, 45(12), 2769–73 (Eng.)]. Several related arylacyrlaryl amides have also been disclosed [Wolfbeis, Otto S., *Chem. Ber.*, 1981, 114(11), 3471–84] but no criticality of substitution patterns has been disclosed to result in highly active postemergent herbicides such as those disclosed and claimed in this application.

Efforts are constantly being made, however, to find compounds which are equal to or greater in effectiveness than presently existing compounds, or which are more economical to produce.

DESCRIPTION OF THE INVENTION

This invention relates to the production of novel arylacrylaryl amide compounds and their use as herbicides. The novel compounds of this invention have the following structural formula

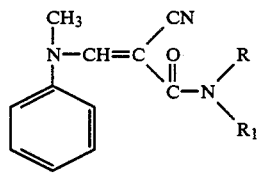

wherein

R is $C_{1-C8}$ aliphatic and cycloaliphatic, $C_2$–$C_3$ haloaliphatic, $C_2$–$C_4$ alkoxyalky, —$CH_2CN$, —$CH(CH_3)CN$ or —$C(CH_3)_2CN$;

$R_1$ is hydrogen or $C_1$–$C_3$ alkyl, provided that R and $R_1$ cannot both equal hydrogen at the same time; or R and $R_1$ taken together form a $C_4$–$C_6$ alkyl or heteroalkyl ring which may be lower alkyl substituted wherein the hetero atom is oxygen or nitrogen.

The above description of the compounds of this invention includes alkyl, alkynyl and alkenyl and includes both straight and branched-chain configurations; including methyl, ethyl, ethenyl, ethynyl, n-propyl, n-propynyl, n-propenyl, isopropyl and isopropenyl.

The compounds of the invention can be produced in a multi-step process in accordance with the following generalized sequence of steps. R and $R_1$ are defined above.

Reaction No. 1

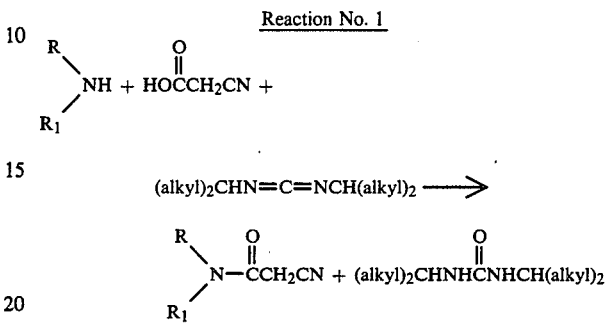

Generally, a 1.1 mole amount of a carbodiimide, dissolved is a one-to-one ratio of tetrahydrofuran and acetonitrile, is added to a mixture of one mole each of the substituted aniline and cyanoacetic acid in the same solvent system. The mixture is stirred at room temperature for about 20 hours. Water (0.1 mole) is added and the mixture filtered. The product is dried over $MgSO_4$, filtered and the solvent evaporated.

Reaction No. 2

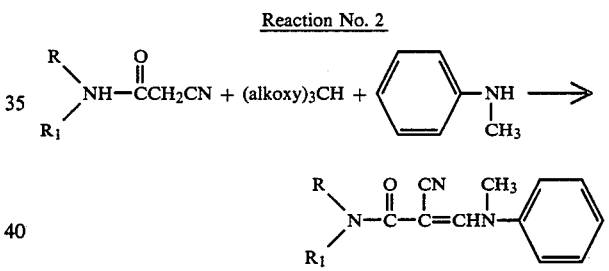

A mole amount each of an arylamine and the reaction product from Reaction No. 1 are combined with 3.5 moles of a trialkoxyorthocarboxylate. The mixture is heated for one hour while low boiling solvent and reaction products are distilled off. The final product is purified by triturating in ether, filtering and air drying.

The example below illustrates methods of making the compounds of the invention using various starting materials. All intermediates and final products were identified by infrared, nuclear magnetic resonance and proton magnetic resonance spectroscopy.

EXAMPLE

Preparation of N-(Cyclopropyl)-3-methylpehnylamino-2-cyanoacetamide

Step 1:

Cyclopropylamine (5.0 grams, 88 mmole) was combined with 7.5 grams (g) (88 mmol) of cyanoacetic acid in 50 milliliters (ml) tetrahydrofuran (THF) and 50 ml $CH_3CN$. Diisopropylcarbodiimide (20 g, 97 mmol) dissolved in 10 ml THF was added dropwise. The reaction mixture exothermed and a white precipitate formed. The mixture was stirred at 20° C. for 20 hours, 5 ml water was added and the reaction mixture was stirred another 5 minutes. The precipitate was filtered off and the filtrate evaporated giving a white solid which was then recrystallized to yield 9.2 g (74 mmol) of N-(cyclopropyl)-2-cyanoacetamide, a white solid (m.p. 104°–106° C.) (84% yield).

Step 2:

Two grams of the product of Step 1 (16 mmol) was combined with 20 ml triethylorthoformate an 2.0 g (18 mmol) of N-methylaniline in a 50 ml flask fitted with a Vigreaux column and distillation head. The mixture was heated for one hour while distillate was collected between 55° and 79° C. Upon cooling the mixture solidified and was then slurried in 25 ml ether, filtered and the solid dried to yield 2.8 g (11 mmol) of the title compound, an orange solid having a melting point of 84°–85° C. The yield was 72%.

This compound will be referred to as Compound No. 1 throughout the remainder of the specification.

The following is a table of certain selected compounds that are preparable according to the procedure described herein. Compound numbers are assigned to each compound and are used throughout the remainder of the application.

TABLE I

| Compound Number | R | $R_1$ | $n_D^{30}$ or melting point °C. |
|---|---|---|---|
| 1 | cyclohexyl | —H | 89–97 |
| 2 | —CH$_2$CH$_2$OCH$_3$ | —H | |
| 3 | —cyclopropyl | —H | 84–85 |
| 4 | —CH(CH$_3$)$_2$ | —H | 134–136 |
| 5 | cyclohexyl | —CH$_3$ | |
| 6 | —CH$_2$CH(CH$_3$)CH$_2$CH(CH$_3$)CH$_2$— | | |
| 7 | (4-methylcyclohexyl) | —H | 86–89 |
| 8 | t-butyl | —H | 57–60 |
| 9 | —CH$_2$—(CH$_2$)$_3$—CH$_2$— | | |
| 10 | —CH$_2$(CH$_2$)$_2$CH$_2$— | | 89–92 |
| 11 | —CH$_2$CH(CH$_3$)$_2$ | —H | 48–50 |
| 12 | n-propyl | —H | |
| 13 | —CH$_2$CF$_3$ | —H | 126–130 |
| 14 | —CH$_2$CH$_2$OCH$_2$CH$_2$— | | |
| 15 | —CH$_3$ | —CH$_3$ | 79–82 |
| 16 | —CH(CH$_3$)CH(CH$_3$)$_2$ | —H | |
| 17 | —C(CH$_3$)$_2$CN | —H | |
| 18 | —CH(CH$_3$)CH$_2$CH$_2$CH(CH$_3$)— | | |
| 19 | —CH$_2$CN | —H | 169–171 |

As previously mentioned, the herein described compounds produced in the above-described manner are phytotoxic compounds which are useful and valuable in controlling various plant species. Selected compounds of this invention were tested as herbicides in the following manner.

POST-EMERGENCE HERBICIDE TEST

Seven grass and broadleaf weed species, including green foxtail (FT) (*Setaria viridis*), watergrass (WG) (*Echinochloa crus-galli*), wild oat (WO) (*Avena fatua*), annual morningglory (AMG) (*Ipomoea purpurea*), velvetleaf (VL) (*Abutilon theophrasti*), mustard (MD) (*Brassica kaber*) and curly dock (CD) (*Rumex crispus*), are seeded in individual rows in 6×10×3 inch flats. The flats are placed in the greenhouse, watered daily (both before and after chemical treatment) with a sprinkler and maintained at about 78° F. Chemical spray treatment is made 12 days after planting. The spray is prepared by weighing out 333 mg of compound and dissolving it in 25 ml acetone containg 1% polyoxyethylene sorbitan monolaurate emulsifier. From this stock solution 18 ml are removed and brought up to a 40 ml volume with a 19:1 water/acetone mixture. The carrier volume is 80 gallons/A (748 L/ha) and a 4 lb/A (4.48 kg/ha) rate is used.

Watering of the treated flats is confined to the soil surface and not to the foilage of the sprouted plants. Twelve to fourteen days after treatment, the degree of injury or control is determined by comparison with untreated "check" plants of the same age. The injury rating from 0 to 100% is recorded for each species as percent control with 0% representing no injury and 100% representing complete control.

The results of the post-emergence herbicide test are reported in Table II.

TABLE II

| | Post-Emergence Herbicidal Activity Application Rate 4.48 kg/ha | | | | | | | | |
|---|---|---|---|---|---|---|---|---|---|
| Cmpd. No. | FT | WG | WO | AMG | VL | MD | CD | AVE GR | AVE BL |
| 1 | 100 | 100 | 100 | 100 | 100 | 100 | 100 | 100 | 100 |
| 2 | 40 | 20 | 20 | 60 | 60 | 40 | 80 | 27 | 60 |
| 3 | 40 | 60 | 0 | 65 | 100 | 100 | 30 | 33 | 74 |
| 4 | 100 | 100 | 85 | 90 | 100 | 100 | 100 | 95 | 98 |
| 5 | 80 | 100 | 65 | 70 | 60 | 100 | 85 | 82 | 79 |
| 6 | 80 | 60 | 35 | 50 | 20 | 60 | 60 | 58 | 48 |
| 7 | 100 | 20 | 25 | 100 | 100 | 100 | 100 | 48 | 100 |
| 8 | 100 | 100 | 100 | 100 | 100 | 100 | 100 | 100 | 100 |
| 9 | 100 | 60 | 100 | 100 | 100 | 100 | 70 | 87 | 93 |
| 10 | 100 | 65 | 100 | 100 | 100 | 100 | 100 | 88 | 100 |
| 11 | | | | | | | | | |
| 12 | 100 | 0 | 20 | 90 | 100 | 100 | 100 | 40 | 98 |
| 13 | 100 | 90 | 90 | 70 | 100 | 100 | 100 | 93 | 93 |
| 14 | 70 | 0 | 60 | 100 | 80 | 100 | 0 | 43 | 70 |
| 15 | 100 | 65 | 100 | 100 | 100 | 100 | 100 | 88 | 100 |
| 16 | 100 | 85 | 100 | 95 | 100 | 100 | 100 | 95 | 99 |
| 17 | 30 | 10 | 0 | 95 | 15 | 90 | 20 | 13 | 55 |
| 18 | 100 | 98 | 100 | 95 | 100 | 100 | 70 | 99 | 91 |
| 19 | 35 | 20 | 0 | 10 | 25 | 50 | 0 | 18 | 21 |

AVE GR = The average of all grass weeds treated at the application rate.
AVE BL = The average of all broadleaf weeds treated at the application rate.

The compounds of the present invention are useful as herbicides, especially as post-emergence herbicides, and can be applied in a variety of ways at various concentrations. In practice, the compounds herein defined are formulated into herbicidal compositions, by admixture, in herbicidally effective amounts, with the adjuvants and carriers normally employed for facilitating the disperson of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for post-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the weeds either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable formulation is ultimately applied to the soil as a dispersion in water or other liquid. These granules are dust-free and free flowing when dry and yet upon dilution in water, form homogeneous dispersions. Typical carriers for dry flowable include fuller's earth, kaolin clays, silicas and other readily available wet organic or inorganic diluents. The dry flowables normally are prepared to contain 5% to about 95% of the active ingredient and usually contains a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and/or other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or other petroleum fractions, or vegetable oils; and/or stickers such as dextrins, glue or synthetic resins.

Typical wetting, dispersing or emulsifying agents used in agricultural formulation include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

| EXAMPLES OF TYPICAL FORMULATIONS | | | |
|---|---|---|---|
| Ingredient | Weight % | | |
| Oil | | | |
| Compound 1 | 1 | | |
| Oil solvent-heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Compound 3 | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredients | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers and other herbicides, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof, triazine derivatives, such as 2,4-bis(3-methoxypropylamino)-6-methylthio-s-triazine, 2-chloro-4-ethylamino-6-isopropylamino-s-triazine, and 2-ethylamino-4-isopropyl-amino-6-methyl-mercapto-s-triazine; urea derivatives, such as 3-(3,5-dichlorophenyl)-1,1-dimethylurea and 3-(p-chlorophenyl)-1,1-dimethylurea; and acetamides such as N,N-diallyl-α-chloroacetamide, and the like; benzoic acids such as 3-amino-2,5-dichlorobenzoic acid; thiocarbamates such as S-propyl N,N-dipropylthiocarbamate, S-ethyl N,N-dipropylthiocarbamate, S-ethyl cyclohexylethylthiocarbamate, S-ethyl hexahydro-1H-azepine-1-carbothioate and the like; anilines such as 4-(methylsulfonyl)-2,6-dinitro-N,N-substituted aniline, 4-trifluoromethyl-2,6-dinitro-N,N-di-n-propyl aniline, 4-trifluoromethyl-2,6-dinitro-N-ethyl-N-butyl aniline, 2-[4-(2,4-dichlorophenoxy)phenoxy]propanoic acid, 2-[1-(ethoxyimino)-butyl]-5-[2-ethylthio)propyl]-3-hydroxy-2-cyclohexene-1-one, (±)-butyl-2-[4-[(5-trifluoromethyl)-2-pyridinyl)oxy]phenoxy]propanate, sodium 5-[2-chloro-4-(trifluoromethyl)phenoxy]-2-nitrobenzoate, 3-isopropyl-1H-2,1,3-benzothiadiazine-4(3H)-one-2,2-dioxide, and 4-amino-6-tert-butyl-3-(methylthio)-as-triazin-5(4H)-one or (4-amino-6-(1,1-dimethylethyl)-3-(methylthio)-1,24-triazin-5(4H)-one. Fertilizers useful in combination with the active ingredients include, for example, ammonium nitrate, urea and superphosphate. Other useful additaments include materials in which plant organisms take root and grow such as compost, manure, humus, sand and the like.

We claim:

1. A compound having the structural formula

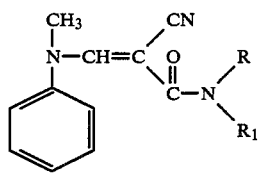

wherein
R is selected from the group consisting of $C_1-C_8$ aliphatic and cycloaliphatic, $C_2-C_3$ haloaliphatic, $C_2-C_4$ alkoxyalkyl, —CH$_2$CN, —CH(CH$_3$)CN and —C(CH$_3$)$_2$CN; and
R$_1$ is selected from the group consisting of hydrogen and $C_1-C_3$ alkyl, provided that both R and R$_1$ cannot both equal hydrogen at the same time.

2. The compound of claim 1 wherein R is chlorine and R$_1$ is hydrogen.

3. The compound of claim 1 wherein R is cyclopropyl and R$_1$ is hydrogen.

4. The compound of claim 1 wherein R is isopropyl and R$_1$ is hydrogen.

5. The compound of claim 1 wherein R is cyclohexyl and R$_1$ is methyl.

6. The compound of claim 1 wherein R is

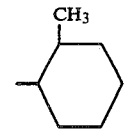

and R$_1$ is hydrogen.

7. The compound of claim 1 wherein R is t-butyl and R$_1$ is hydrogen.

8. The compound of claim 1 wherein R and R$_1$ together are —CH$_2$(CH$_2$)$_3$CH$_2$—.

9. The compound of claim 1 wherein R and R$_1$ together are —CH$_2$(CH$_2$)$_2$CH$_2$—.

10. The compound of claim 1 wherein R is —CH$_2$CH(CH$_3$)$_2$ and R$_1$ is hydrogen.

11. The compound of claim 1 wherein R is n-propyl and R$_1$ is hydrogen.

12. The compound of claim 1 wherein R is —CH$_2$CF$_3$ and R$_1$ is hydrogen.

13. The compound of claim 1 wherein R is methyl and R$_1$ is methyl.

14. The compound of claim 1 wherein R is —CH(CH$_3$)CH(CH$_3$)$_2$ and R$_1$ is hydrogen.

15. The compound of claim 1 wherein R and R$_1$ together are —CH(CH$_3$)CH$_2$CH$_2$CH(CH$_3$)—.

16. A herbicidal composition comprising an herbicidally effective amount of a compound having the structural formula

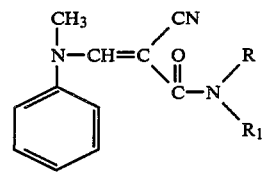

wherein
R is selected from the group consisting of $C_1-C_8$ aliphatic and cycloaliphatic, $C_2-C_3$ haloaliphatic, $C_2-C_4$ alkoxyalkyl, -CH$_2$CN, —CH(CH$_3$)CN and —C(CH$_3$)$_2$CN; and
R$_1$ is selected from the group consisting of hydrogen and $C_1-C_3$ alkyl, provided that both R and R$_1$ cannot both equal hydrogen at the same time; and an inert carrier.

17. The method of controlling undesirable vegetation comprising applying to the area where control is desired, an herbicidally effective amount of a compound having the formula

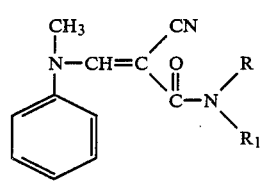

wherein

R is selected from the group consisting of $C_1$–$C_8$ aliphatic and cycloaliphatic, $C_2$–$C_3$ haloaliphatic, $C_2$–$C_4$ alkoxyalkyl, —CH$_2$CN, —CH(CH$_3$)CN and —C(CH$_3$)$_2$CN; and R$_1$ is selected from the group consisting of hydrogen and $C_1$–$C_3$ alkyl, provided that both R and R$_1$ cannot both equal hydrogen at the same time.

18. The method of claim 17 wherein R is chlorine and R$_1$ is hydrogen.

19. The method of claim 17 wherein R is cyclopropyl and R$_1$ is hydrogen.

20. The method of claim 17 wherein R is isopropyl and R$_1$ is hydrogen.

21. The method of claim 17 wherein R is cyclohexyl and R$_1$ is methyl.

22. The method of claim 17 wherein R is

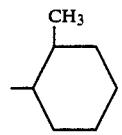

and R$_1$ is hydrogen.

23. The method of claim 17 wherein R is t-butyl and R$_1$ is hydrogen.

24. The method of claim 17 wherein R and R$_1$ together are —CH$_2$(CH$_2$)$_3$CH$_2$—.

25. The method of claim 17 wherein R and R$_1$ together are —CH$_2$(CH$_2$)$_2$CH$_2$—.

26. The method of claim 17 wherein R is —CH$_2$CH(CH$_3$)$_2$ and R$_1$ is hydrogen.

27. The method of claim 17 wherein R is n-propyl and R$_1$ is hydrogen.

28. The method of claim 17 wherein R is —CH$_2$CF$_3$ and R$_1$ is hydrogen.

29. The method of claim 17 wherein R is methyl and R$_1$ is methyl.

30. The method of claim 17 wherein R is —CH(CH$_3$)CH(CH$_3$)$_2$ and R$_1$ is hydrogen.

31. The method of claim 17 wherein R and R$_1$ together are —CH(CH$_3$)CH$_2$CH$_2$CH(CH$_3$)—.

* * * * *